US012788718B2

(12) United States Patent
Katepalli et al.

(10) Patent No.: US 12,788,718 B2
(45) Date of Patent: Nov. 10, 2026

(54) USE OF PEG-BASED INTERPOLYMER COMPLEXES FOR IMPROVED SOLUBILIZATION F BCS CLASS II DRUGS

(71) Applicant: Dow Global Technologies LLC, Midland, MI (US)

(72) Inventors: Hari Katepalli, Midland, MI (US); Thomas H. Kalantar, Midland, MI (US); Xue Chen, Manvel, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 109 days.

(21) Appl. No.: 18/842,870

(22) PCT Filed: May 17, 2023

(86) PCT No.: PCT/US2023/067088
§ 371 (c)(1),
(2) Date: Aug. 30, 2024

(87) PCT Pub. No.: WO2023/225533
PCT Pub. Date: Nov. 23, 2023

(65) Prior Publication Data

US 2025/0064733 A1 Feb. 27, 2025

Related U.S. Application Data

(60) Provisional application No. 63/343,587, filed on May 19, 2022.

(51) Int. Cl.

| | |
|---|---|
| ***A61K 9/08*** | (2006.01) |
| ***A61K 31/10*** | (2006.01) |
| ***A61K 31/192*** | (2006.01) |
| ***A61K 47/10*** | (2017.01) |
| ***A61K 47/32*** | (2006.01) |

(52) U.S. Cl.
CPC ................ *A61K 9/08* (2013.01); *A61K 31/10* (2013.01); *A61K 31/192* (2013.01); *A61K 47/10* (2013.01); *A61K 47/32* (2013.01)

(58) Field of Classification Search
None
See application file for complete search history.

(56) References Cited

U.S. PATENT DOCUMENTS

2020/0170957 A1* 6/2020 Leleti ................... A61K 9/4825

FOREIGN PATENT DOCUMENTS

| | | |
|---|---|---|
| CA | 364742 | 3/1937 |
| RU | 2435584 | 12/2011 |

OTHER PUBLICATIONS

Int. J. Pharm., 2007, vol. 334, pp. 15-26 (Year: 2007).*
Kanaujia, "Amorphous formulations 1-10 for dissolution and bioavailability enhancement of poorly soluble APIs", Powder Technology, 2015, vol. 285, pp. 2-15.
Khutoryanskiy, "Hydrogen-bonded interpolymer complexes as materials for pharmaceutical applications", International Journal of Pharmaceutics, 2007, vol. 334, is. 1-2, pp. 15-26.
Sareen, "Improvement in solubility of poor water-soluble drugs by solid dispersion", International Journal of Pharmaceutical Investigation, 2012, vol. 2, No. 1, pp. 12.

* cited by examiner

*Primary Examiner* — Brian Gulledge

(57) ABSTRACT

The present invention comprises a method of improving the water-solubility of an active pharmaceutical ingredient which has been classified as being in class II of the Biopharmaceutics Classification System. The method comprises mixing a polyethylene glycol with a polyacrylic acid in water under conditions sufficient to form at least some inter-polymer complex, and then adding the active pharmaceutical ingredient to the mixture.

9 Claims, No Drawings

USE OF PEG-BASED INTERPOLYMER COMPLEXES FOR IMPROVED SOLUBILIZATION F BCS CLASS II DRUGS

FIELD

The present invention comprises a method of improving the water-solubility of an active pharmaceutical ingredient which has been classified as being in class II of the Biopharmaceutics Classification System.

BACKGROUND AND SUMMARY

Solubility, dissolution, and gastrointestinal permeability are basic parameters that control the rate and extent of drug absorption and its bioavailability. The aqueous solubility of the drug plays an important role in drug absorption after oral administration. Inadequate aqueous solubility of active pharmaceutical ingredients is very challenging in the development process of new drug formulations. Poor water solubility obstructs drug bioavailability and decreases its pharmaceutical development. Pharmaceutical development of drugs with poor water solubility requires the establishment of a suitable formulation layout among various techniques. An estimated 40-80% of new drug candidates are active but insoluble and increasing their solubility or bioavailability is a long-standing goal of the global pharma industry. Many drug excipient materials form solid dispersion with drug actives, leading to development of amorphous forms of the drug that have an increased apparent solubility in water and an increased dissolution rate. This is desirable in order to increase the bioavailability of Active Pharmaceutical Ingredients ("APIs") with low solubility but high permeability, and which are classified in the Biopharmaceutics Classification System ("BCS") as class II drugs.

Various methods to improve the aqueous solubility and poor dissolution rate of BCS class II drugs have been studied and include the use of hydrotropes, complexation, solid dispersion, salt formation, emulsification, co-crystallization, and nano-crystal technologies. Previous studies indicate that polyethylene glycol (PEG) on its own is often not very efficient at stabilizing the amorphous form of drugs and PEG can generate brittle and hard crystal formulations.

The present invention considers a new type of carrier based on the formation of inter-polymer complexes of PEG with polyacrylic acid (PAA), which is another FDA-approved excipient polymers/material, to enable higher apparent aqueous solubility and more rapid dissolution of BCS class II APIs.

Inter-polymer complexes (or IPCs), as generally known in the art, are the products of non-covalent interactions between complementary unlike macromolecules in solutions and in the solid state. There are four generally recognized types of these complexes: Interpolyelectrolyte complexes (IPEC) or polyelectrolyte complexes (PEC); Hydrogen-bonded interpolymer complexes; Stereocomplexes; and Charge-transfer complexes. The hydrogen bonded interpolymer complexes are thought to be particularly relevant to the present invention. Interpolymer complexes can be prepared either by mixing complementary polymers in solution or by matrix (template) polymerization. It is also possible to prepare IPCs at liquid-liquid interfaces or at solid or soft surfaces. Usually, the structure of the IPCs formed will depend on many factors, including the nature of the interacting polymers, concentrations of their solutions, nature of the solvent, presence of inorganic ions or organic molecules in solutions, etc.

It has been discovered that the use of PEG+PAA based IPCs as excipients for BCS class II drugs will result in the solubility enhancement for those drugs, defined by having an apparent solubility improvement by >100% over that of pure BCS class II API or that of the formulation with PEG alone in preliminary evaluation, and the ability to maintain supersaturation of the drug in aqueous solution for at least 30 minutes.

DETAILED DESCRIPTION

The present invention comprises a method of improving the water-solubility of an active pharmaceutical ingredient which has been classified as being in class II of the Bipopharmaceutics Classification System. The method comprises mixing a polyethylene glycol (PEG) with a polyacrylic acid (PAA) in water under conditions sufficient to form at least some inter-polymer complex, and then adding the active pharmaceutical ingredient to the mixture.

The polyethylene glycol (PEG) preferably has a molecular weight of at least 1500 g/mol, 2000 g/mol, 2500 g/mol or even 3000 g/mol. The polyethylene glycol preferably has a molecular weight of less than 10,000 g/mol, 9,500 g/mol, 9,000 g/mol or even 8,500 g/mol.

The polyacrylic acid (PAA) has a molecular weight has a molecular weight of at least 800 g/mol, 1,000 g/mol, 1,250 g/mol or even 1,500 g/mol. The polyacrylic acid preferably has a molecular weight of less than 4,000 g/mol, 3,500 g/mol, 3,000 g/mol or even 2,500 g/mol.

Suitable conditions for forming at least some IPC between the polyethylene glycol and the polyacrylic acid are mixing the PEG and PAA together with water at room temperature. The ratio of PEG to PAA in such mixture can be from 1:1 to 1:2. The total amount of polymer in such an aqueous solution can be from 0.25, 0.5, 0.75 or 1.0 percent by weight up to 5, 4, 3, or 2 percent by weight, with around 1 percent by weight being generally preferred. While the mixing is preferred to be conducted at room temperature due to the ease of the process, it will be readily understood that other temperatures can be used, with slightly elevated temperatures even leading to quicker formation of the IPC. An active pharmaceutical ingredient which has been classified as being in class II of the Biopharmaceutics Classification System is then added to the resulting aqueous solution comprising the polyethylene glycol and the polyacrylic acid, that is, the resulting IPC. The API can be any class II material, such as Probucol or Ketoprofen. Preferably some sort of agitation is used, such as mechanical stirring, shaking, aspiration, etc., to help the API go into solution.

Depending on the API chosen, it may be beneficial to first dissolve the API in a solvent prior to, or simultaneously with the aqueous IPC solution. Water-soluble organic solvents can be used for this purpose, including alcohols, tertrahydrofuran, dimethyl sulfoxide, dimethylformamide, etc. Alcohols, particularly methanol, ethanol, propanol, isopropanol, butanol, isobutanol, and t-butanol, are preferred solvents for this purpose. For example, solutions of the API in methanol at a concentration of from 10 g/L, 15 g/L or 20 g/L up to 40 g/L 34 g/L or 30 g/L may be advantageously used.

The amount of API added to such aqueous IPC solution will depend in part on the particular API and the amount of polymer in the solution. The effectiveness of the present method can be determined by comparing the increase in apparent solubility of the API in an aqueous solution as well as the ability to maintain the elevated saturation levels for 30 minutes or more. Apparent solubility is the ratio of solubility of the active pharmaceutical ingredient in presence of IPC forming mixture to the solubility of the active pharmaceutical ingredient in water without any additives. Preferably the apparent solubility will be increased by at least 100%, 200%, 250% or even 300%, even when measured after allowing the solutions to sit for at least 30 minutes. The apparent solubility is preferably maintained at approximately the same levels for at least 30 minutes, or even 60 minutes. For the purposes of this invention, the term "approximately the same levels" means that the solubility remains within at least 10 percent of the original measured values.

EXAMPLES

To demonstrate the efficacy of the present invention a series of experiments can be run. The following materials are used. The polyacrylic acid (PAA) has a molecular weight of about 1800, the polyethylene glycol used has either a molecular weight of 4000 or 8000 (as indicated in Table I below). The API chosen is either Probucol (>98% purity) or Ketoprofen (>98% purity). Each polymer or polymer combination shown in Table 1 is added to water in an amount to form 1% polymer solutions. Concentrated API solutions in methanol are prepared by adding 0.2 grams of drug to 10 ml of methanol (20 g/L of drug in methanol).

For each example in Table 1, 912 μl of the indicated polymer solution is transferred into individual vials. Then, 48 μl of drug solution in methanol is added to the polymer solution. These mixtures are agitated via three cycles of aspiration and dispensing using the EVO 200 pipettes.

The samples are then allowed to sit for thirty minutes, After thirty minutes each sample is cetrifuged 13600 rpm for 10 min, and a 30 μL aliquot from the supernatant for each sample is taken and diluted with 150 μL methanol for HPLC analysis.

The solubilized drug concentration in each taken aliquot was determined by reverse phase high-performance liquid chromatography (HPLC) analysis. For this purpose, 2 μL of the respective diluted taken aliquot were injected to an Agilent 1100 HPLC system equipped with a reversed-phase XDB-C8 column The drug concentration is determined from the measured elution profile by using a linear calibration curve for the respective drug, which was generated by determining the least squares fit of a straight line that described the relation between the concentration of four solutions of known concentrations (about 250, 500, 750, and 1000 mg/L) and the respective peak area integral after injection of 2 μL of each drug in methanol. Each example was run in triplicate and the results are averaged and reported in Table 1.

For comparative reasons the afore-mentioned test procedure is performed analogously with the drug added to water without any polymer dissolved therein.

TABLE 1

| Example | Excipient | Probucol solubility (mg/L) [a, b] | Increase in probucol solubility[c] |
|---|---|---|---|
| control | none | ~0 (0.042) | ~0 |
| Comp 1 | PAA 1800 | 8.07 | ~192 |
| Comp 2 | PEG 4000 | 0.49 | ~11 |
| Comp 3 | PEG 8000 | 0.93 | ~22 |
| Inv 1 | PAA 1800:PEG 4000(1:1) | 12.84 | ~305 |
| Inv 2 | PAA 1800:PEG 4000(1:2) | 12.24 | ~291 |
| Inv 3 | PAA 1800:PEG 8000(1:1) | 17.28 | ~411 |
| Inv 4 | PAA 1800:PEG 8000(1:2) | 19.84 | ~472 |

[a] The ratio drug/excipient = 1:12 (wt./wt.) in all samples;
[b] Average values from three measurements using HPLC method;
[c] Increase relative to the aqueous probucol solubility of 0.042 mg/L.

As shown in Table 1, using the IPC as provided for in the present invention, solubility of the API in an aqueous solution is greatly improved over pure water, PAA alone and even PEG alone.

The invention claimed is:

1. A method of improving the water-solubility of an active pharmaceutical ingredient which has been classified as being in class II of the Biopharmaceutics Classification System comprising a. mixing a polyethylene glycol with a polyacrylic acid in water under conditions sufficient to allow at least some inter-polymer complex to form;

b. adding the active pharmaceutical ingredient to the mixture; and wherein the active pharmaceutical ingredient is Probucol or Ketoprofen.

2. The method of claim 1 where the polyacrylic acid has a molecular weight in the range of from 1000 to 3000.

3. The method of claim 1 where the polyethylene glycol has a molecular weight in the range of from 2000 to 10,000.

4. The method of claim 1 wherein the polyethylene glycol and the polyacrylic acid are mixed before the addition of the active pharmaceutical ingredient.

5. The method of claim 4 wherein the aqueous solution comprises from 0.5 to 2.5% by weight of the inter-polymer complex.

6. The method of claim 1 where the active pharmaceutical ingredient is added to a solvent prior to adding to the aqueous mixture of polyethylene glycol and polyacrylic acid.

7. The method of claim 6 wherein the solvent is an alcohol having from 1 to 4 carbon atoms.

8. The method of claim 6 where the active pharmaceutical ingredient is added to the solvent in an amount of from 1 gram per liter solvent to 100 grams per liter of solvent.

9. The method of claim 1 wherein the solubility of the active pharmaceutical ingredient in water with the inter polymer complex is improved by greater than 200 percent as compared to the solubility of active ingredient in water alone.

* * * * *